US009885695B2

(12) United States Patent
Nakatani et al.

(10) Patent No.: US 9,885,695 B2
(45) Date of Patent: Feb. 6, 2018

(54) GAS ANALYSIS DEVICE

(75) Inventors: Shigeru Nakatani, Kyoto (JP); Kenji Hara, Kyoto (JP); Montajir Rahman, Otsu (JP); Masahiro Nakane, Kyoto (JP)

(73) Assignee: Horiba, Ltd., Kyoto (JP)

( * ) Notice: Subject to any disclaimer, the term of this patent is extended or adjusted under 35 U.S.C. 154(b) by 419 days.

(21) Appl. No.: 14/004,097

(22) PCT Filed: Feb. 9, 2012

(86) PCT No.: PCT/JP2012/052951
§ 371 (c)(1),
(2), (4) Date: Sep. 9, 2013

(87) PCT Pub. No.: WO2012/120957
PCT Pub. Date: Sep. 13, 2012

(65) Prior Publication Data
US 2014/0002823 A1    Jan. 2, 2014

(30) Foreign Application Priority Data
Mar. 9, 2011    (JP) .................................. 2011-052231

(51) Int. Cl.
*G01N 33/00*    (2006.01)
*G01N 21/3504*    (2014.01)
(Continued)

(52) U.S. Cl.
CPC ......... *G01N 33/0009* (2013.01); *G01N 21/05* (2013.01); *G01N 21/15* (2013.01);
(Continued)

(58) Field of Classification Search
CPC ......... G01N 3032/115; G01N 33/0029; G01N 33/0009; G01N 2021/151
See application file for complete search history.

(56) References Cited

U.S. PATENT DOCUMENTS 3,035,903 A * 5/1962 Rand, Jr. .................. G01N 7/04
422/88
3,512,393 A * 5/1970 Weiss .................... G01N 1/2258
73/23.2
(Continued)

FOREIGN PATENT DOCUMENTS

DE    102005016320 A1    10/2006
JP    10104133    4/1998
(Continued)

OTHER PUBLICATIONS

Office Action dated Jan. 5, 2016 issued for Japanese Patent Application No. 2013-503424, 4 pgs.

*Primary Examiner* — Tri Ton
*Assistant Examiner* — Rebecca C Bryant
(74) *Attorney, Agent, or Firm* — Brooks Kushman P.C.

(57) ABSTRACT

In order to be able to prevent analysis accuracy from being reduced by a backward flow of sample gas from dead volume in a cleaning mechanism into a cell at the time of analysis, a gas analysis device has an analysis part that analyzes the sample gas introduced into the cell, gas ports that are arranged toward predetermined regions of gas contact surfaces in the cell, and a piping mechanism that connects the gas ports to a predetermined purge gas source, and blows purge gas from the gas ports toward the predetermined regions at the time of purging. The gas analysis device also has a switching part that switches a connecting destination of the piping mechanism from the purge gas source to a predetermined suction part, and at the time of introducing or analyzing the sample gas, connects the gas ports to the suction source.

8 Claims, 4 Drawing Sheets

(51) Int. Cl.
*G01N 21/05* (2006.01)
*G01N 21/15* (2006.01)

(52) U.S. Cl.
CPC ..... *G01N 21/3504* (2013.01); *G01N 33/0029* (2013.01); *G01N 2021/151* (2013.01)

(56) References Cited

U.S. PATENT DOCUMENTS

| | | | | |
|---|---|---|---|---|
| 3,897,211 | A | * 7/1975 | Ririe, Jr. | ............ G01N 33/0011 422/89 |
| 6,458,213 | B1 | 10/2002 | Krieg et al. | |
| 6,748,334 | B1 | * 6/2004 | Perez | ................ G01N 21/3504 702/24 |
| 2010/0149538 | A1 | 6/2010 | Fleischer et al. | |

FOREIGN PATENT DOCUMENTS

| | | |
|---|---|---|
| JP | 2001159587 | 6/2001 |
| JP | 2001-311686 A | 11/2001 |
| JP | 2002-277395 A | 9/2002 |
| JP | 2002277361 | 9/2002 |
| JP | 2003-021627 A | 1/2003 |
| JP | 2005331309 | 12/2005 |
| JP | 2009-175058 A | 8/2009 |

* cited by examiner

GAS ANALYSIS DEVICE

CROSS-REFERENCE TO RELATED APPLICATIONS

This application is the U.S. national phase of PCT App. No. PCT/JP2012/052951, filed Feb. 9, 2012, which claims priority to Japanese App. No. 2011-052231, filed Mar. 9, 2011, the disclosure of which is incorporated in its entirety by reference herein.

TECHNICAL FIELD

The present invention relates to a gas analysis device for analyzing sample gas introduced into a cell.

BACKGROUND ART

In the case of making various types of analyses on sample gas, the sample gas is introduced into a cell where measurements are made, and the analyses by various types of analysis parts are made on the sample gas in the cell (see JP 2001-159587). For example, in the case of measuring the concentration of component gas contained in the sample gas on the basis of absorbance, the measurement is made by making a laser beam incident into the cell, and detecting the laser beam that returns outside of the cell after repetitive reflection by a multiple reflection mirror arranged inside the cell.

In such measurement, if dirt adheres to an object having a gas contact surface contacted by the sample gas in the cell, such as the multiple reflection mirror or a cell inner wall surface, due to a component contained in the sample gas, analysis accuracy is spoiled. To overcome this, there is a device that is adapted to, by arranging a gas port toward a predetermined region of the gas contact surface that influences the analysis accuracy, and connecting the gas port to a predetermined purge gas source through a piping mechanism, blow purge gas from the gas port toward the gas contact surface to remove the dirt on the gas contact surface.

However, if a configuration for cleaning the gas contact surface as described above is added, there may occur a problem at a time other than the time of the gas purging for cleaning. Specifically, in the case of not introducing the purge gas, such as at the time of introducing or analyzing the sample gas, the sample gas intrudes from the gas port into the piping mechanism due to an effect of diffusion or the like, and therefore the sample gas is accumulated in dead volume inside the piping mechanism. If the sample gas accumulated in the piping mechanism returns into the cell at the time of the analysis for some reason, a parameter of the sample gas currently present in the cell, such as concentration, is changed, and as a result, accurate measurement may be prevented. In particular, if adsorptive gas such as NH3 is contained in the sample gas, the adsorptive gas adheres to an inner surface of the piping mechanism to accumulate much more gas, and therefore a measurement error is likely to increase.

SUMMARY OF INVENTION

Technical Problem

Therefore, the present invention is made in consideration of the problem as described above, and intended to provide a gas analysis device that can, while introducing a cleaning mechanism for removing dirt on a gas contact surface, prevent analysis accuracy from being reduced by a backward flow of sample gas from dead volume inside the cleaning mechanism into a cell at the time of analysis.

Solution to Problem

That is, a gas analysis device comprising: a cell into which sample gas is introduced; an analysis part that analyzes the sample gas introduced into the cell; a gas port that is arranged toward a predetermined region of a gas contact surface in the cell; and a piping mechanism that connects the gas port to a predetermined purge gas source, and is configured to blow purge gas from the gas port toward the predetermined region at a time of purging that cleans the gas contact surface, wherein the gas analysis device further comprising a switching part that switches a connecting destination of the piping mechanism from the purge gas source to a predetermined suction source, and configured to, at a time of introducing or analyzing the sample gas, connect the gas port to the suction source.

If so, even in the case of providing the gas port for blowing the purge gas to clean the gas contact surface, the gas analysis device is configured to, at the time of introducing or analyzing the sample gas, connect the gas port to the suction source, and therefore the sample gas never flows back from inside of the piping mechanism into the cell. That is, even in the case where the sample gas is accumulated in a part serving as dead volume in the piping mechanism, no change occurs in a parameter of the sample gas present in the cell, such as concentration, and therefore a reduction in analysis accuracy can be prevented.

Further the switching part only switches the connecting destination of the piping mechanism from the purge gas source to the predetermined suction source, and therefore even without providing a complicated mechanism in the cell, a backward flow from the gas port into the cell can be prevented to increase the analysis accuracy.

In order to, even in the case where by making the sample gas keep flowing into the cell at the time of the analysis, suctioning is performed from the gas port, reduce an influence on an absolute amount of the sample gas to further increase the analysis accuracy, it is only necessary that the cell comprising: an introduction port for introducing the sample gas; and, a discharge port for discharging the sample gas, wherein both of the introduction port and the discharge port are opened at the time of the analysis.

Configurations that enable accuracy and responsiveness of a detection signal to be kept by at the time of the analysis, reducing an amount of the sample gas sucked from the gas port and discharging as much of the sample gas as possible from the discharge port include one in which a flow rate of the gas sucked from the gas port is set smaller than a flow rate of the gas discharged from the discharge port.

Sample gases that make the above-described effects more remarkable include one in which the sample gas contains adsorptive gas.

Advantageous Effects of Invention

As described, according to the gas analysis device of the present invention, the gas port for blowing the purge gas toward the predetermined region of the gas contact surface is adapted to, not only blow the purge gas but also suck the sample gas at least at the time of the sample gas inflow or the sample gas analysis, and therefore at the time of the analysis, a backward flow of the sample gas accumulated in the piping mechanism connected to the gas port can be prevented to prevent a reduction in analysis accuracy.

REFERENCE SIGNS LIST

Figure 1:
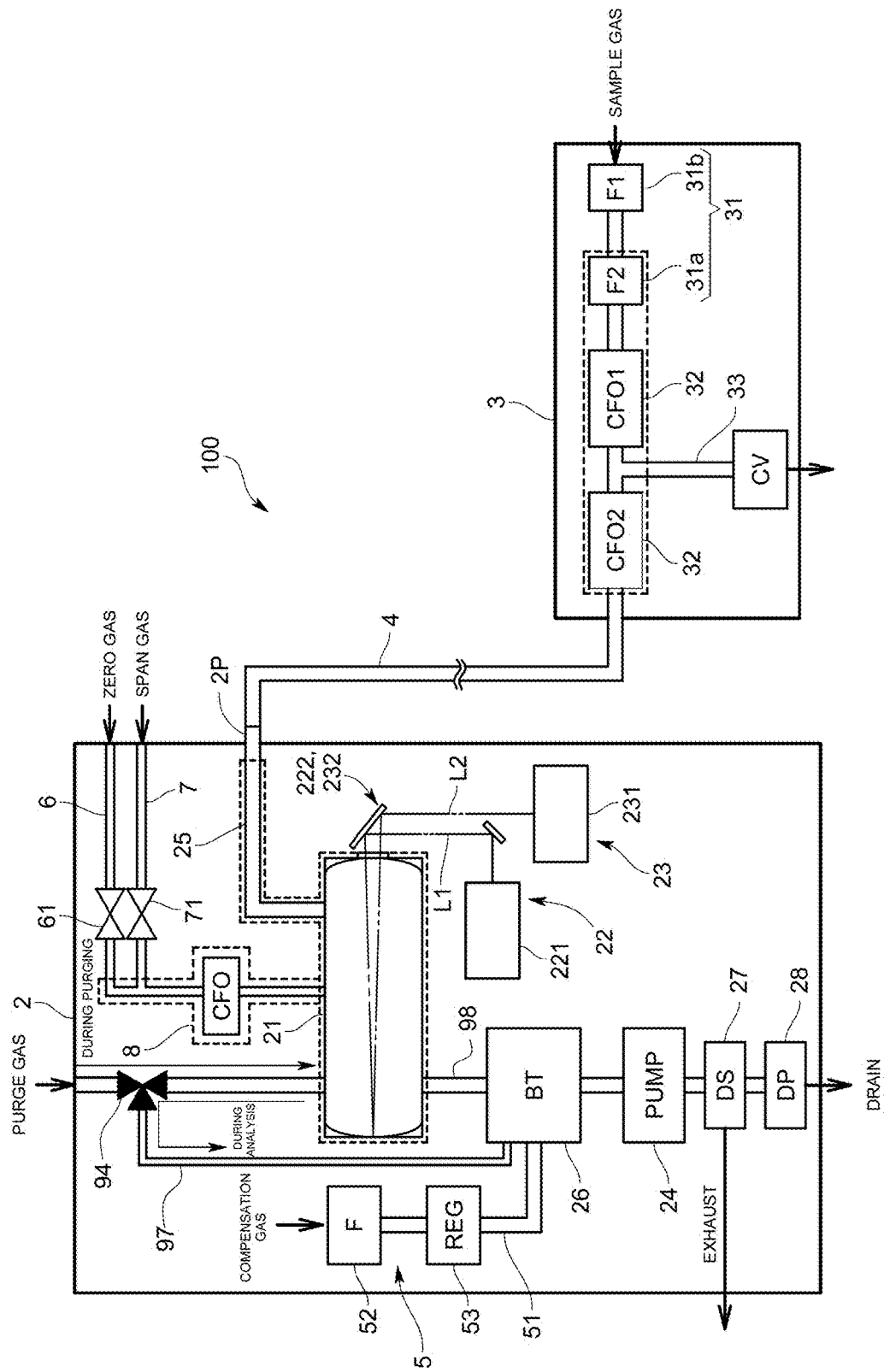
FIG. 1 is a configuration diagram schematically illustrating an exhaust gas analysis device of the present embodiment.

100 Exhaust gas analysis device (gas analysis device)
21 Measuring cell (cell)
22 Laser beam irradiation part (analysis means)
23 Light detection part (analysis part)
91 Gas port
92 Piping mechanism
93 Purge gas source
94 Electromagnetic three way valve (switching part)
95 Introduction port
96 Discharge port

DESCRIPTION OF EMBODIMENTS

In the following, one embodiment of an exhaust gas analysis device 100 according to the present invention is described with reference to the drawings.

An exhaust gas analysis device 100 according to the present embodiment is one that is, for example, connected to an exhaust pipe (tail pipe) of a vehicle or the like, and uses absorption spectrophotometry to measure the concentrations of No, $NO_2$, $N_2O$ and $NH_3$ contained in exhaust gas that is discharged from the exhaust pipe and serves as sample gas.

Specifically, the exhaust gas analysis device 100 is, as illustrated in FIG. 1, provided with: a device main body 2 for measuring the sample gas; a flow rate control unit 3 that is provided as a separate body from the device main body 2 and attached to the exhaust pipe of the vehicle; and a heating pipe 4 that is connected to the device main body 2 and the flow rate control unit 3, and introduces the exhaust gas introduced from the flow rate control unit 3 into the device main body 2. In addition, the device main body 2 and the flow rate control unit 3 are provided in locations different from each other, and without any other casing or the like containing them together, connected to each other only through the heating pipe 4.

Figure 2:
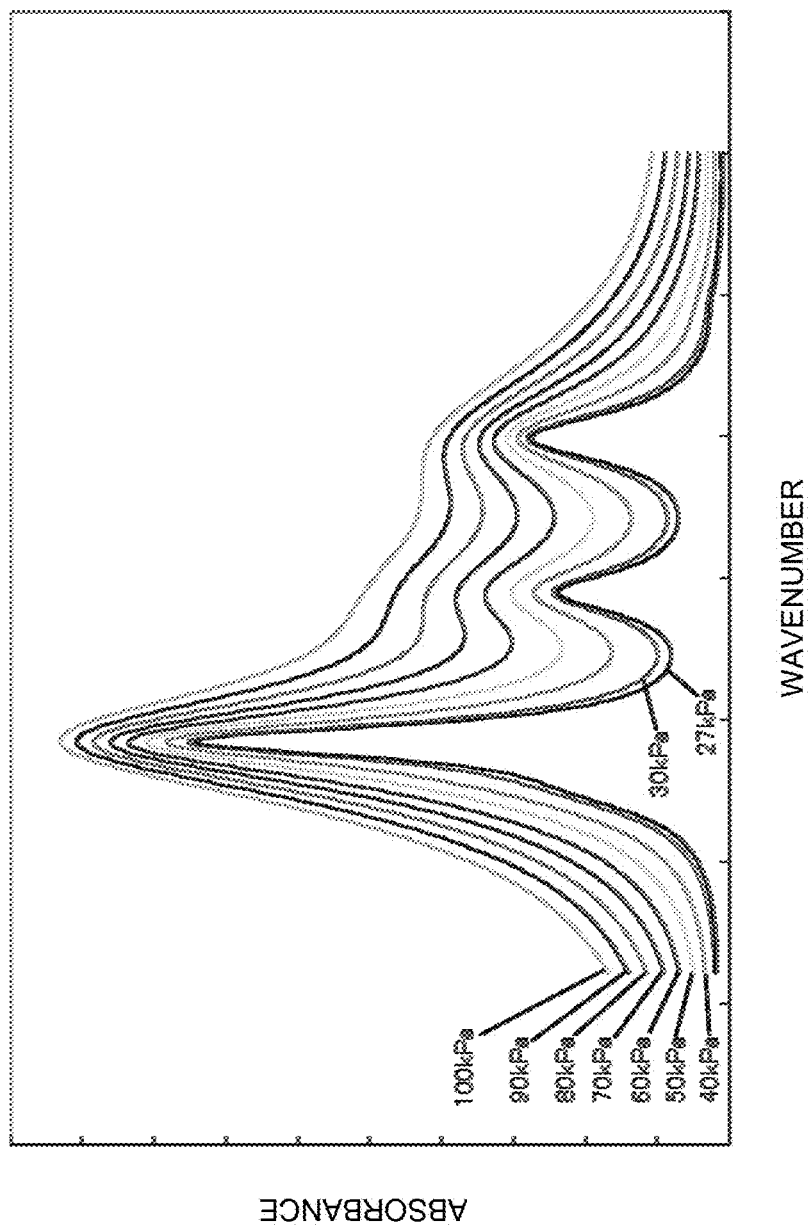
FIG. 2 is a diagram illustrating a pressure variation in absorption spectrum of sample gas having absorptive gases.

The device main body 2 is provided with: a multiple reflection type measuring cell 21 for measuring the sample gas; a laser beam irradiation part 22 that introduces a laser beam L1 from a light introduction window of the measuring cell 21 to irradiate the sample gas in the measuring cell 21 with the laser beam L1 having high linearity; a light detection part 23 that detects a transmitted laser beam L2 exiting from the measuring cell 21; and a negative pressure pump 24 that is connected to the measuring cell 21 and subjects the inside of the measuring cell 21 to negative pressure. Note that the measuring cell 21 is configured to be of a multiple reflection type, and therefore even if a measured component is at low concentration, detection sensitivity can be increased. Also, the negative pressure pump 24 keeps the inside of the measuring pressure at negative pressure within a range of, for example, 1 kPa (pressure at which gas concentration becomes too small and therefore measurement becomes difficult) to 80 kPa (pressure at which a peak becomes gentle and therefore interference with another gas component is likely to occur), and preferably at negative pressure within a range of 20 kPa to 50 kPa that is a pressure range where adsorption of an $NH_3$ component is unlikely to occur, measurable gas concentration is achieved, and further interference with another gas component does not occur. 20 kPa to 50 kPa as described enables both of the measuring cell 21 and the after-mentioned heating pipe 4 to be kept at the same pressure by the one negative pressure pump 24. Note that as illustrated in FIG. 2, in absorption spectra of the sample gas having adsorptive gases component, peaks start to rise at a pressure of 80 kPa or less, and the peaks clearly appear at a pressure of 50 kPa or less.

Further, the device main body 2 is connected with the after-mentioned heating pipe 4, and has an introduction port 2P for introducing the exhaust gas flowing through the heating pipe 4 into the measuring cell 21. The introduction port P2 and the measuring cell 21 are connected to each other through an internal connecting pipe 25. In addition, the introduction port 2P, internal connecting pipe 25, and measuring cell 21 are heated to, for example, 113° C. or 191° C. in order to prevent moisture in the exhaust gas from condensing.

The laser beam irradiation part 22 is provided with: a laser beam source 221 that emits the laser beam L1: and a guide mechanism 222 including components such as a reflective mirror that guides the beam from the laser beam source 221 to the measuring cell 21. Note that, in the present embodiment, $NH_3$ is targeted as one of the adsorptive gas components, and therefore the laser light source 221 is a wavelength tunable laser that emits a laser beam having an oscillating wavelength in an infrared region such as a mid-infrared region or a near infrared region, or in an ultraviolet region, where $NH_3$ exhibits absorption characteristics, and for example, a semiconductor laser such as a quantum cascade laser (QCL) or a wavelength tunable semiconductor laser, a solid state laser, or a liquid laser may be used.

As the laser beam source 221, it is particularly preferable to use the quantum cascade laser (QCL). The QCL element is one that oscillates a laser beam with current pulses having regular intervals, and an oscillation wavenumber from the laser element depends on temperature, so that as a result, the oscillation wavenumber is repetitively scanned within a certain narrow wavenumber range. In the absorption spectrophotometry using the QCL (QCL-IR method), an element of which an oscillation center wavenumber is adjusted is used such that an absorption peak position of the targeted component falls within the range. In addition, as will be described later, in the measuring cell 21 subjected to the negative pressure, density of the sample gas is decreased, and the sensitivity is reduced. However, by using the QCL having an oscillating wavelength (pulse width is 500 nsec) in the mid-infrared region, measurements can be made in the wavelength region where absorbance is large, so that without reducing the sensitivity even under the negative pressure, the concentration of the adsorptive gas component can be measured, and a high speed response becomes possible.

The light detection part 23 is one that detects the transmitted laser beam L2 that exits from the measuring cell 21 after having been multiply reflected in the measuring cell 21, and for example, a room temperature operable MCT (HgCdTe) detector 23 may be used. In addition, between the MCT detector 231 and the measuring cell 21, a guide mechanism 232 including components such as a reflective mirror for guiding the transmitted laser beam L2 to the MCT detector 231 is provided. A light intensity signal obtained by the MCT detector 231 is outputted to an unillustrated arithmetic unit. Then, the arithmetic unit calculates the absorbance of each of the components to perform an operation of the concentration of the component. In addition, the laser beam irradiation part 22 and the light detection part 23 correspond to an analysis part in claims.

The flow rate control unit 3 is one that is connected to the exhaust pipe of the vehicle, and provided with: a filter 31 for removing dust in the exhaust gas discharged from the exhaust pipe; and a flow rate limiting part 32 for limiting a flow rate of the exhaust gas having passing through the filter 31. Also, the flow rate control unit 3 is preferably attached to an exhaust port of the exhaust pipe directly, or to a location within 2 m inclusive from the exhaust port through piping. In particular, the flow rate control unit 3 is more preferably attached to a location within 50 cm inclusive. This enables the exhaust gas discharged from the exhaust pipe to be brought into a negative pressure state on an upstream side in an early stage.

The filter 31 includes: for example, a cylindrical filter 31b that is replaceable by a user and on an upstream side; and for example, a disk-shaped filter 31a that is provided inside the flow rate control unit 3, irreplaceable by the user, and on a downstream side. Also, for the flow rate limiting part 32, a critical orifice (CFO) for decreasing a contact gas area to shorten a response time is used. As described, the flow rate control unit 3 is a unit having the filter 31 and the critical orifice (CFO), and can be downsized.

Specifically, the flow rate limiting part 32 is configured to use two critical orifices CFO1 and CFO2 that are arranged in series, or use only one critical orifice CFO2. Also, between the two critical orifices CFO1 and CFO2, a branched flow path 33 provided with a check valve CV is provided. On the basis of such a configuration, the present embodiment is adapted to, in the case where the exhaust gas flowing through the flow rate control unit 3 is at high pressure, discharge part of the sample gas to the outside from the branched flow path 33. Also, the critical orifice CFO2 on the downstream side is connected with the after-mentioned heating pipe 4. The filter 31 and the flow rate limiting part 32 are heated to, for example, 113° C. or 191° C. in order to prevent moisture in the exhaust gas from condensing.

The heating pipe 4 is one that makes a connection between the device main body 2 and the flow rate control unit 3 that are respectively provided as separate bodies, and configured such that around a pipe, a heater is wound. Specifically, the heating pipe 4 is connected to the introduction port 2P of the device main body 2 on a downstream side thereof, and connected to the flow rate limiting part 32 (specifically, CFO2) of the flow rate control unit 3 on an upstream side thereof.

Also, the heating pipe 4 heats the exhaust gas having passed through the flow rate control unit 3 to 100° C. to 200° C. to lead the exhaust gas to the introduction port 2P of the device main body 2. Note that, if the heating temperature is lower than 100° C., the adsorptive gas components such as the $NH_3$ gas are likely to adsorb or condense in the heating pipe 4. On the other hand, if the heating temperature is higher than 200° C., in the case of forming the heating pipe 4 with use of, for example, fluorine resin (PTFE), the PTFE may be melted. In the present embodiment, the exhaust gas is heated to 113° C. or 191° C., which is the same temperature as the heating temperature for the measuring cell 21, and led to the introduction port 2P of the device main body 2. On the basis of such a configuration, the present embodiment is configured to provide an upstream side end part of the heating pipe 4 with the flow rate limiting part 32.

In addition, as a material for the pipe of the heating pipe 4, stainless steel (SUS), fluorine resin (PTFE), or the like is possible; however, in order to reduce the adsorption of $NH_3$ to shorten the response time, it is preferable to use the fluorine resin (PTFE). Further, in the case of using stainless steel (SUS), by coating an inner surface of the heating pipe 4 with porous material such as porous silicon, the $NH_3$ gas substantially made up of polar molecules may be adsorbed. Also, by performing surface treatment or mirror polishing on the inner wall surface of the heating pipe 4, the adsorption can be further reduced.

Figure 3:
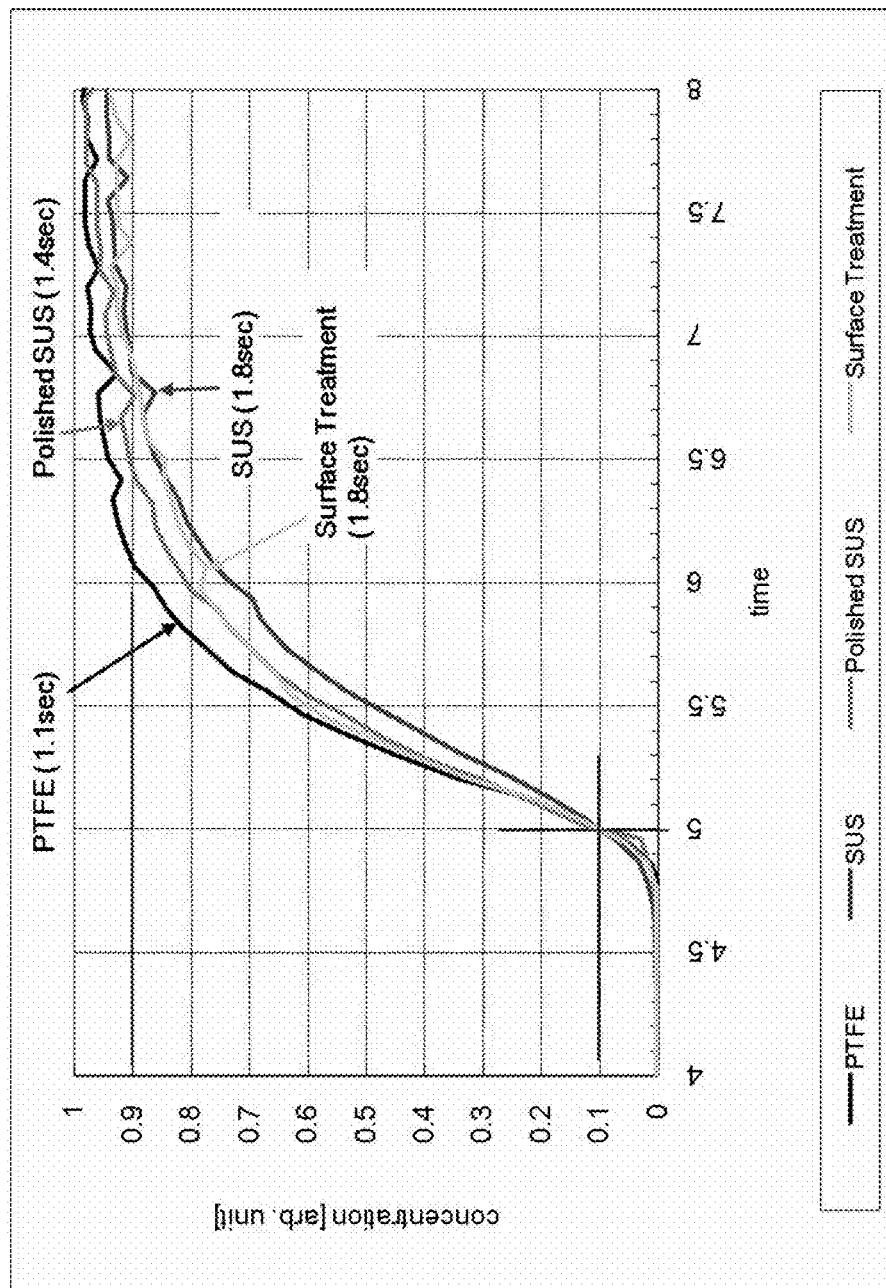
FIG. 3 illustrates experimental results on a response time in the cases of using various types of heating pipes.

Here, experimental results on the response time in the cases of (1) using the fluorine resin (PTFE), (2) using normal stainless steel (SUS), (3) using mirror-polished stainless steel (SUS), and (4) using surface-treated stainless steel (SUS) are illustrated in FIG. 3. In addition, FIG. 3 illustrates the results of measuring 50 ppm $NH_3$ gas under the conditions of a sample flow rate of 10 L/min, a sample pipe length of 2 m, and a pipe temperature of room temperature (approximately 25° C.). Also, the response time in the diagram refers to a time from $T_{10}$ (measurement time indicating a concentration of 10%) to $T_{90}$ (measurement time indicating a concentration of 90%). As can be seen from FIG. 3, the response times respectively corresponding to the various types of heating pipes are 1.1 seconds for the PTFE pipe, 1.8 seconds for the normal SUS pipe, 1.4 seconds for the mirror-polished SUS pipe, and 1.8 seconds for the surface-treated SUS pipe. From these results, it turns out that the use of the PTFE pipe is most advantageous from the perspective of response time.

Also, in the exhaust gas analysis device 100 of the present embodiment, from the start of sampling to the end of the measurement, the negative pressure pump 24 connected to the measuring cell 21 subjects the inside of the measuring cell 21 to the negative pressure as well as subjecting the flow path from a downstream side of the flow rate limiting part 32 (specifically, CFO2) to the measuring cell 21 to the negative pressure. That is, the negative pressure pump 24 subjects the flow path from the measuring cell 21 to the flow rate limiting part 32 through the heating pipe 4 to the negative pressure that is substantially the same pressure (e.g., 25 kPa) as that in the measuring cell 21. In the present embodiment, the flow path from the downstream side of the flow rate limiting part 32 (specifically, CFO2) to the measuring cell 21 includes a flow path inside the heating pipe 4, a flow path inside the introduction port 2P, and a flow path inside the internal connecting pipe 25 that connects the introduction port 2P and the measuring cell 21 to each other.

In addition, the measuring cell 21 is connected with: a zero gas pipe 6 that, in order to make a zero point adjustment of the exhaust gas analysis device 100 (specifically, the light detection part 23), supplies zero gas to the measuring cell 21; and a span gas pipe 7 that, in order to make a span adjustment of the exhaust gas analysis device 100 (specifically, the light detection part 23), supplies span gas into the measuring cell 21. The zero gas pipe 6 and the span gas pipe 7 are respectively provided with on/off valves 61 and 71 for switching supply of the gases, such as solenoid valves. Also, the zero gas pipe 6 and the span gas pipe 7 join together on an upstream side of a critical orifice (CFO) 8 serving as a flow rate limiting element, and are supplied into the measuring cell 21 through the critical orifice 8. Note that the critical orifice 8 is heated to, for example, 113° C. or 191°

C., as with the flow rate limiting part 32 of the flow rate control unit 3. This enables the zero adjustment and the span adjustment to be made under the same conditions as measurement conditions.

Further, the measuring cell 21 is one that is further provided with a cleaning mechanism 9 for blowing purge gas toward predetermined regions of gas contact surfaces contacted by the sample gas in the measuring cell 21 to remove dirt and the like in the predetermined regions. A configuration of the cleaning mechanism 9 will be described later in detail.

Also, between the negative pressure pump 24 and the measuring cell 21, a buffer tank 26 is provided. The present embodiment is configured to, on the basis of the buffer tank 26, prevent a flow rate of the sample gas introduced into the measuring cell 21 from being varied by pulsation of the negative pressure pump 24. In addition, on a downstream side of the negative pressure pump 24, a drain separator 27 and a drain pot 28 are connected. The exhaust gas separated from a drain by the drain separator 27 is discharged outside from the drain separator 27. Also, the drain separated from the gas by the drain separator 27 is contained in the drain pot 28 and then discharged.

Further, the flow rate limiting part 32 of the flow rate control unit 3 serves as a critical orifice, and only the negative pressure pump 24 cannot regulate pressure of the sample gas introduced into the measuring cell 21. For this reason, in the present embodiment, a flow rate pressure regulating mechanism 5 for regulating the pressure of the sample gas introduced into the measuring cell 21 is provided. The flow rate pressure regulating mechanism 5 is connected to a connecting pipe between the negative pressure pump 24 and the measuring cell 21, and provided with: a flow path 51 that introduces compensation gas such as the air; a filter 52 that is provided in the flow path 51; and a regulator 53 for regulating a flow rate of the compensation gas, such as a pressure regulating valve. The regulator 53 regulates pressure of the compensation gas so as to subject the inside of the measuring cell 21 to a given pressure. Note that, in a path from the exhaust pipe to the measuring cell 21, no regulator is provided, and therefore there is no possibility of the adsorption of $NH_3$ by a regulator. In addition, in the present embodiment, the flow path 51 is connected to the buffer tank 26.

OVERALL EFFECTS OF PRESENT EMBODIMENT

According to the exhaust gas analysis device 100 according to the present embodiment configured as described, the flow rate limiting part 32 is provided at the upstream side end part of the heating pipe 4 provided outside of the device main body 2, and the negative pressure pump 24 subjects the inside of the measuring cell 21 and the flow path from the downstream side of the flow rate limiting part 32 to the measuring cell 21 to the negative pressure, so that a region subjected to the negative pressure can be made as large as possible in a flow path connecting to the measuring cell 21 to reduce the adsorption of the $NH_3$ component. Also, the flow rate limiting part 32 is provided, and also the negative pressure pump 24 achieves a state of keeping the negative pressure from the start of the sampling to the end of the measurement, so that the downstream side of the flow rate limiting part 32 can be prevented from being subjected to positive pressure by inflow pressure of the sample gas, and therefore the $NH_3$ component can be prevented from adhering. This enables the $NH_3$ component to be measured with accuracy even in the case where the $NH_3$ component is at low concentration, and further a response speed of the concentration measurement to be improved. Note that once the $NH_3$ component adsorbs, the $NH_3$ component is unlikely to come out, and therefore as described above, it is necessary to constantly keep the negative pressure from the start of the sampling to the end of the measurement.

Also, at the upstream side end part of the heating pipe 4, the flow rate limiting part 32 is provided, so that the sample gas subjected to the negative pressure is heated, and therefore a dissolution loss of the $NH_3$ component due to condensation in the heating pipe 4 can be further prevented.

In addition, it is known that when observing an absorption spectrum at room temperature, an absorption peak has broadening; however, by bringing the inside of the measuring cell 21 into the negative pressure state, sharper peaks can be obtained, and therefore an influence of interference on an absorption peak of the $NH_3$ component can be reduced.

<Details of Configurations of Measuring Cell 21 and Cleaning Mechanism 9 of Present Embodiment>

Figure 4:
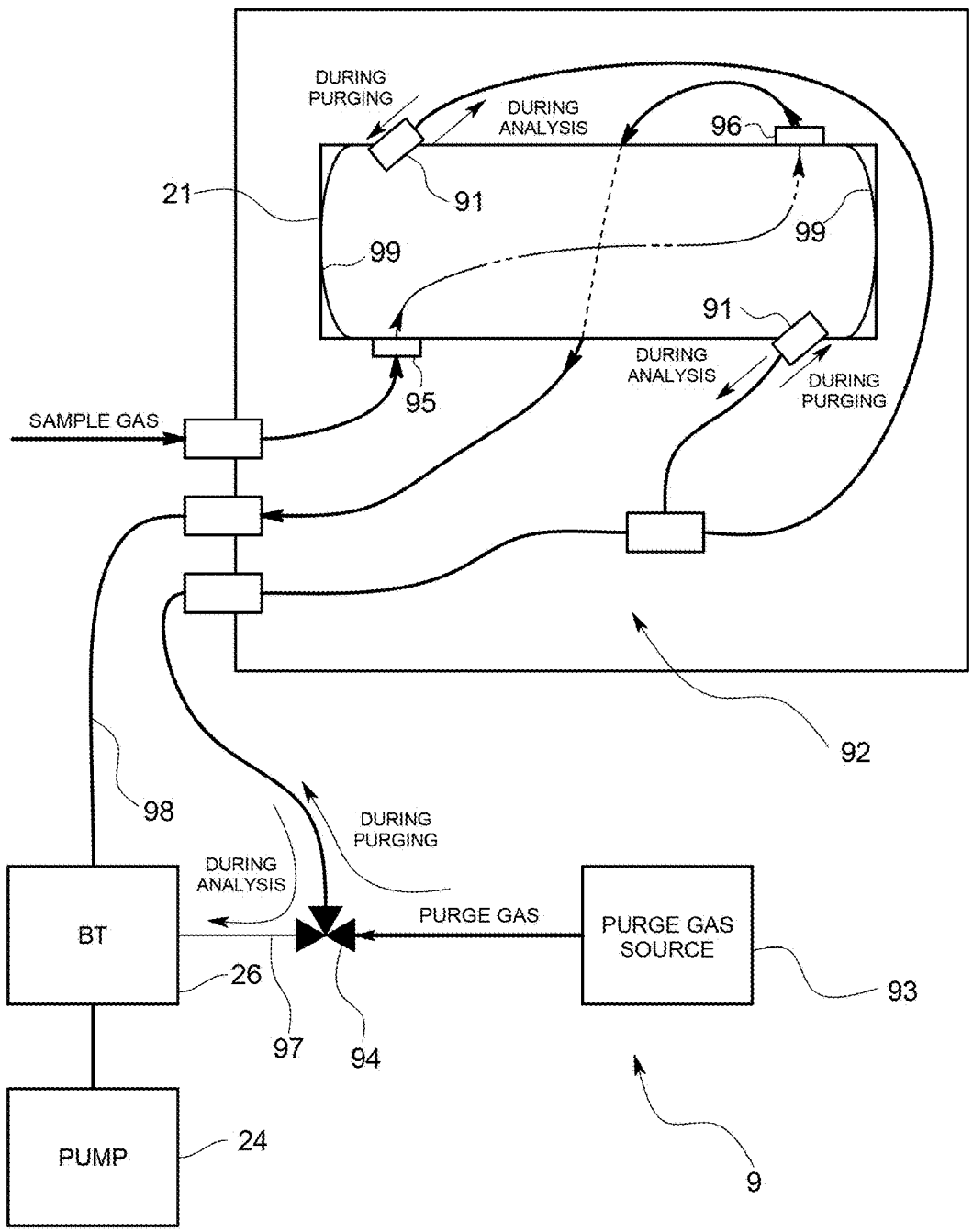
FIG. 4 is a detailed diagram where the periphery of a measuring cell in the exhaust gas analysis device of the present embodiment is enlarged.

Here, the measuring cell 21 and the cleaning mechanism 9 are described in more detail with reference to FIG. 4 that is a diagram where the periphery of the measuring cell 21 is enlarged.

The measuring cell 21 is one having a schematically hollow and rectangular parallelepiped shape, and in the diagram view, is, on respective end surfaces thereof, provided with multiple reflection mirrors 99 for multiply reflecting the laser beam. In the cross-sectional view of FIG. 4, near the multiple reflection mirrors 99, an introduction port 95 for introducing the sample gas into the cell, and a discharge port 96 for discharging the sample gas are diagonally provided. Also, the introduction port 95 and the discharge port 96 are configured to, at the time of the analysis, both open to thereby circulate the sample gas in the cell. Note that "both open" refers to the concept that both of the introduction port 95 and the discharge port 96 may be constantly opened, or may be temporarily closed except during the analysis and opened only during the analysis. The introduction port 95 is adapted to be connected to the flow rate control unit 3 through piping to introduce the sample gas into the measuring cell 21. The discharge port 96 is adapted to be connected to the after-mentioned measuring cell 21 and the negative pressure pump 24 to discharge the sample gas in the measuring cell 21 to the outside. The present embodiment is adapted such that, by connecting and arranging the introduction port 95 and the discharge port 96 as described, the sample gas introduced into the measuring cell 21 moves to the discharge port 96 while meandering between the respective multiple reflection mirrors 99 as indicated by a schematic imaginary line.

Next, the cleaning mechanism 9 provided for the measuring cell 21 is described. The cleaning mechanism 9 is one that is intended to blow the purge gas to remove dirt so as to prevent the dirt from continuing to adhere to the multiple reflection mirrors 99 due to components contained in the sample gas. More specifically, the cleaning mechanism 9 is one that is provided with: gas ports 91 that are provided for the measuring cell 21 so as to be able to blow the purge gas toward the predetermined regions of the gas contact surfaces in the measuring cell 21; a piping mechanism 92 that, at least at the time of the purging, connects the gas ports 91 and a purge gas source 93 to each other; and an electromagnetic three way valve 94 that is switching means adapted to switch a connecting destination of the piping mechanism 92 from the purge gas source 93 to a predetermined suction source.

The two gas ports 91 are ones that are, in order to enable the purge gas to be blown toward concave surfaces of the respective multiple reflection mirrors 99, provided for the measuring cell 21. The two gas ports 91 are, in the diagram view, provided in top and bottom surfaces of the measuring cell 21, and the respective gas ports 91 are diagonally arranged as well as being arranged so as to face to the introduction port and the discharge port 96 on opposite surface sides. That is, the introduction port, the discharge port 96, and the respective gas ports 91 are arranged at the four corners when seeing the measuring cell 21 in a vertical cross section.

One piping flow path of the piping mechanism 92 is one that connects the respective gas ports 91 and the predetermined purge gas source 93 to each other through the electromagnetic three way valve 94, and at the time of the purging, adapted to enable the purge gas supplied from the purge gas source 93 to be blown toward the multiple reflection mirrors 99. Specific examples of the purge gas include air not containing water, and inert gases such as Ar and $N_2$, each of which pressure blows adhering dirt to perform cleaning. Also, the present invention may be adapted to use reactive gas such as $NO_2$ or $O_3$ as the purge gas to chemically break down and remove adhering soot. On the other hand, the other piping flow path of the piping mechanism 92 is one that connects the gas ports 91 and the negative pressure pump 24 serving as the suction source of the present embodiment to each other through the electromagnetic three way valve 94.

The electromagnetic three way valve 94 is configured to, at the time of the purging, open/close so as to connect only the gas ports 91 and the purge gas source 93 to each other, and at the time of introducing the sample gas into the measuring cell 21 or at the time of the analysis, connect only the gas ports 91 and the negative pressure pump 24 to each other through the after-mentioned buffer tank 26. Also, a diameter of a pipe 97 that connects the electromagnetic three way valve 94 and the buffer tank 26 to each other is set smaller as compared with a diameter of a pipe 98 that makes a connection from the discharge port 96 for discharging the sample gas from inside the measuring cell 21 to the buffer tank 26, and a flow rate of the gas sucked from the gas ports 91 is set smaller than a flow rate of the gas discharged from the discharge port 96. In other words, a relationship between the flow rate of the gas sucked from the discharge port 96 and the flow rate of the gas sucked from the gas ports 91 is set so as to achieve a relationship that can keep a state where the sample gas is uniformly dispersed in the measuring cell 21.

<Effects Due to Measuring Cell 21 and Cleaning Mechanism 9 of Present Embodiment>

In the case where the blowing of the purge gas toward the multiple reflection mirrors 99 as described above is not performed, in particular, at the time of the analysis, the electromagnetic three way valve 94 is switched to connect the gas ports 91 and the negative pressure pump 24 to each other, and therefore gases such as the sample gas accumulated in the piping mechanism 92 can be prevented from flowing back into the measuring cell 21 through the gas ports 91. Accordingly, an error can be prevented from occurring in the concentration measurement of $NH_3$ or the like due to a change in concentration of the sample gas in the measuring cell 21, or due to the inflow of an additional component. Further, the flow rate of the gas sucked from the gas ports 91 is set smaller than the flow rate of the sample gas discharged from the discharge port 96, and therefore a situation that a large amount of sample gas is sucked from the gas ports 91 without passing between the multiple reflection mirrors 99 can be prevented to measure absorbance of any of substantially all sample gases. Accordingly, intensity of the signal outputted from the light detection part 23 can be increased to make concentration measurements with separating the respective gas components from one another.

<Other Variations>

Note that the present invention is not limited to the above-described embodiment.

For example, as a configuration in which the flow rate control part is arranged at the upstream side end part of the heating pipe, the above-described embodiment is configured to maximize flow path volume subjected to the negative pressure; however, besides, the present invention may be adapted to make provision on the heating pipe.

Also, for the flow rate control part, in addition to the critical orifice, a vacuum regulator such as a pressure regulation valve, a capillary, or a venture may be used.

Further, in the above-described embodiment, as one of the adsorptive gas components, the $NH_3$ component is described; however, besides, the present invention may be adapted to analyze a highly adsorptive gas component such as a hydrocarbon (HC) component. Examples of the hydrocarbon (HC) component include aromatic hydrocarbons such as toluene, alcohols such as methanol and ethanol, high boiling HCs, and the like. Also, as the highly adsorptive gas component, a polar molecule such as $NO_2$, $SO_2$, or $H_2O$ is cited. In addition, in the above-described embodiment, the device main body 2 and the flow rate control unit 3 are configured to be separate bodies, but need not be separate bodies.

In addition, the measuring cell is a so-called flow cell into and out of which the sample gas flows; however, the measuring cell may be a batch type cell in which the sample gas is accumulated once and analyzed without being flowed out. Even in such a cell, in the case of providing the gas ports in order to remove dirt on gas contact surfaces in the measuring cell, at the time of the analysis or introducing the sample gas, the sample gas accumulated in a part serving as dead volume in the piping mechanism may return into the measuring cell to adversely influence analysis accuracy. In order to prevent such a situation, even in the batch type measuring cell, it is only necessary to enable the connecting destination of the gas ports and the piping mechanism to be switched from the purge gas source to the suction source by the switching part.

Also, the above-described embodiment is adapted to be able to make an object used as a power source for introducing the sample gas from the introduction port serve as the suction source for performing the suctioning from the gas ports, and share the object; however, the present invention may be further provided with a suction source separately.

In the above-described embodiment, as the predetermined regions of the gas contact surfaces, the multiple reflection mirrors are set; however, the present invention may set other regions. Specifically, the present invention may be configured to set an inner wall of the measuring cell, holders of the multiple reflection mirrors, or a sensor (such as a temperature sensor) that measures an internal state of the measuring cell as at least one of the predetermined regions of the gas contact surfaces to remove dirt with the purge gas. Also, as another example, the present invention may set directions of the gas ports so as to be able to regularly flow the purge gas toward locations likely to form sample gas accumulation spots due to internal structure of the measuring cell, or other locations.

In addition, the configuration of the cleaning mechanism is particularly effective in the case where adsorptive gas such as NH 3 is contained in sample gas; however, even for other gas, the configuration of the cleaning mechanism is useful to improve analysis accuracy. Also, the above-described analysis part may be one that measures other characteristic values, and not limited to the laser light source or light detection part.

Besides, it should be appreciated that the present invention is not limited to the above-described embodiment, but can be variously modified without departing from the scope thereof.

INDUSTRIAL APPLICABILITY

As described above, according to the gas analysis device of the present invention, the gas ports for blowing the purge gas toward the predetermined regions of the gas contact surfaces are adapted to, not only blow the purge gas, but also suck the sample gas at least at the time of the sample gas inflow or the sample gas analysis, and therefore at the time of the analysis, a backward flow of the sample gas accumulated in the piping mechanism connected to the gas ports can be prevented to prevent a reduction in analysis accuracy.

The invention claimed is:

1. A gas analysis device comprising:
   a cell having an inner surface that contacts a sample gas introduced into the cell;
   an analysis part configured to analyze the sample gas introduced into the cell;
   an introduction port configured to introduce the sample gas into the cell;
   a discharge port configured to discharge the sample gas from the cell;
   a purge gas port oriented toward a predetermined region of a gas contact surface in the cell, wherein the introduction port, the discharge port, and the purge gas port are each formed on the cell at different locations;
   a switching part; and
   a piping mechanism fluidly connecting the purge gas port to the switching part, wherein the switching part is configured, at a time of purging, to fluidly connect the purge gas port to a predetermined purge gas source via the piping mechanism such that the predetermined purge gas source blows purge gas through the purge gas port toward the predetermined region to clean the gas contact surface, and at a time of introducing or analyzing the sample gas by introducing the sample gas into the cell through the introduction port and discharging the sample gas from the cell through the discharge port, to fluidly connect the purge gas port to a predetermined suction source via the piping mechanism such that the predetermined suction source sucks gas through the purge gas port from the cell.

2. The gas analysis device according to claim 1, wherein both of the introduction port and the discharge port are opened at the time of the analyzing.

3. The gas analysis device according to claim 2, wherein a flow rate of gas sucked from the cell through the purge gas port is set smaller than a flow rate of gas discharged from the discharge port.

4. The gas analysis device according to claim 1, wherein the sample gas contains adsorptive gas.

5. A gas analysis method using a gas analysis device including a cell having an inner surface that contacts a sample gas introduced into the cell, an analysis part configured to analyze the sample gas introduced into the cell, an introduction port configured to introduce the sample gas into the cell, a discharge port configured to discharge the sample gas from the cell, a purge gas port oriented toward a predetermined region of a gas contact surface in the cell, a switching part, and a piping mechanism fluidly connecting the purge gas port to the switching part, wherein the introduction port, the discharge port, and the purge gas port are each formed on the cell at different locations, the method comprising:
   at a time of purging, operating by a controller the switching part to fluidly connect the purge gas port to a predetermined purge gas source via the piping mechanism such that the predetermined purge gas source blows purge gas through the purge gas port toward the predetermined region to clean the gas contact surface; and
   at a time of introducing or analyzing the sample gas by introducing the sample gas into the cell through the introduction port and discharging the sample gas from the cell through the discharge port, operating by the controller the switching part to fluidly connect the purge gas port to a predetermined suction source via the piping mechanism such that the predetermined suction source sucks gas through the purge gas port from the cell.

6. The gas analysis method according to claim 5, wherein the cell includes an introduction port configured to introduce the sample gas and a discharge port configured to discharge the sample gas, further comprising opening both of the introduction port and the discharge port at the time of the analyzing.

7. The gas analysis method according to claim 6 further comprising connecting the purge gas port and the discharge port to the suction source via the piping mechanism, and setting a diameter of a part of a pipe between the purge gas port and the suction source smaller than a diameter of a pipe between the discharge port and the suction source.

8. The gas analysis method according to claim 5, wherein the sample gas contains adsorptive gas.

* * * * *